US008476212B2

(12) United States Patent
Decoster et al.

(10) Patent No.: US 8,476,212 B2
(45) Date of Patent: Jul. 2, 2013

(54) DETERGENT COSMETIC COMPOSITIONS COMPRISING AT LEAST ONE AMINO SILICONE, AND USES THEREOF

(75) Inventors: Sandrine Decoster, Saint Gratien (FR); Stéphanie Neplaz, Paris (FR)

(73) Assignee: L'Oreal, Paris (FR)

(*) Notice: Subject to any disclaimer, the term of this patent is extended or adjusted under 35 U.S.C. 154(b) by 84 days.

(21) Appl. No.: 12/498,582

(22) Filed: Jul. 7, 2009

(65) Prior Publication Data
US 2010/0068165 A1 Mar. 18, 2010

Related U.S. Application Data

(60) Provisional application No. 61/129,641, filed on Jul. 9, 2008.

(30) Foreign Application Priority Data
Jul. 8, 2008 (FR) ..................... 08 54634

(51) Int. Cl.
C11D 1/94 (2006.01)
C11D 9/36 (2006.01)

(52) U.S. Cl.
USPC ........... 510/124; 510/119; 510/122; 510/123; 510/125; 510/127; 510/130; 510/426; 510/427; 510/466; 510/490

(58) Field of Classification Search
USPC ................ 510/119, 122, 123, 124, 125, 127, 510/130, 426, 427, 466, 490
See application file for complete search history.

(56) References Cited

U.S. PATENT DOCUMENTS

| 3,950,417 | A | | 4/1976 | Verdicchio et al. |
| 6,033,652 | A | * | 3/2000 | Ansmann .................. 424/70.122 |
| 6,153,569 | A | | 11/2000 | Halloran |
| 6,159,914 | A | | 12/2000 | DeCoster et al. |
| 6,475,499 | B2 | | 11/2002 | Maubru et al. |
| 6,726,902 | B1 | | 4/2004 | Muller et al. |
| 6,808,701 | B2 | | 10/2004 | Duden et al. |
| 6,824,764 | B2 | | 11/2004 | Devin-Baudoin et al. |
| 6,824,765 | B2 | | 11/2004 | Gawtrey et al. |
| 7,179,452 | B2 | | 2/2007 | Muller et al. |
| 2001/0009909 | A1 | | 7/2001 | Maubru et al. |
| 2002/0006389 | A1 | | 1/2002 | Restle et al. |
| 2003/0108501 | A1 | | 6/2003 | Hofrichter et al. |
| 2003/0129155 | A1 | * | 7/2003 | Devin-Baudoin et al. ... 424/70.2 |
| 2003/0134760 | A1 | | 7/2003 | Harrison et al. |
| 2003/0157049 | A1 | * | 8/2003 | Gawtrey et al. .......... 424/70.122 |
| 2004/0170593 | A1 | | 9/2004 | Muller et al. |
| 2004/0258653 | A1 | * | 12/2004 | Sakai et al. ................. 424/70.31 |
| 2005/0019299 | A1 | * | 1/2005 | LiBrizzi et al. ............ 424/70.17 |
| 2005/0063934 | A1 | | 3/2005 | Baker et al. |
| 2005/0232885 | A1 | | 10/2005 | Samain et al. |
| 2006/0019858 | A1 | * | 1/2006 | Kruse et al. .................... 510/424 |
| 2006/0275245 | A1 | * | 12/2006 | Decoster et al. ......... 424/70.122 |
| 2007/0009461 | A1 | * | 1/2007 | Chandra et al. .............. 424/70.1 |
| 2007/0041930 | A1 | | 2/2007 | Meder et al. |
| 2007/0077221 | A1 | * | 4/2007 | Seigneurin et al. ........ 424/70.16 |
| 2007/0258936 | A1 | * | 11/2007 | Decoster et al. ............ 424/70.12 |
| 2008/0171684 | A1 | * | 7/2008 | Boutique et al. ............... 510/299 |
| 2008/0276385 | A1 | * | 11/2008 | Cottard et al. ..................... 8/408 |
| 2008/0311066 | A1 | * | 12/2008 | Samain et al. ............. 424/70.16 |
| 2009/0000638 | A1 | * | 1/2009 | Wood et al. .................... 132/205 |
| 2009/0074699 | A1 | * | 3/2009 | Biganska et al. .......... 424/70.16 |
| 2009/0130028 | A1 | * | 5/2009 | Rollat-Corvol et al. ........ 424/47 |

FOREIGN PATENT DOCUMENTS

| EP | 0 453 238 | 10/1991 |
| EP | 0 697 206 | 2/1996 |
| EP | 0 870 491 | 10/1998 |
| EP | 0 974 335 | 1/2000 |
| EP | 1 136 066 | 9/2001 |
| EP | 1 312 345 | 5/2003 |
| EP | 1 312 346 | 5/2003 |
| EP | 1 321 131 | 6/2003 |
| EP | 1 543 820 | 6/2005 |
| EP | 1 726 294 | 11/2006 |
| EP | 1 726 295 | 11/2006 |
| EP | 1 849 453 | 10/2007 |
| FR | 2 785 181 | 5/2000 |
| FR | 2 804 020 | 7/2001 |
| FR | 2 864 767 | 7/2005 |
| WO | WO 95/26707 | 10/1995 |
| WO | WO 2006/065469 | 6/2006 |

OTHER PUBLICATIONS

Anonymous, "Cosmetic Raw Materials," Clariant Personal Care Brochure, (2006).
Copending Application titled "Detergent Cosmetic Compositions Comprising an Amino Silicone, and Use Thereof," filed Jul. 7, 2009, Inventors: Sandrine Decoster et al.
English language Abstract of EP 1 321 131, dated Jun. 25, 2003.
English language Abstract of EP 1 726 294, dated Nov. 29, 2006.
English language Abstract of EP 1 726 295, dated Nov. 29, 2006.
French Search Report for FR 08/54633, dated Mar. 4, 2009.
French Search Report for FR 08/54634, dated Mar. 5, 2009.
Copending U.S. Appl. No. 11/790,936, filed Apr. 30, 2007.
English language Abstract of EP 0 697 206, dated Feb. 21, 1996.
French Search Report for FR 06/03848, dated Dec. 20, 2006.
Office Action mailed Dec. 22, 2010, in co-pending U.S. Appl. No. 12/498,625.
Office Action mailed Nov. 27, 2009, in co-pending U.S. Appl. No. 11/790,936.
Office Action mailed Sep. 9, 2010, in co-pending U.S. Appl. No. 11/790,936.
Office Action mailed Aug. 11, 2011, in co-pending U.S. Appl. No. 12/498,625.

* cited by examiner

Primary Examiner — Charles Boyer
(74) Attorney, Agent, or Firm — O'Brien Jones, PLLC.

(57) ABSTRACT

The disclosure relates to novel detergent compositions comprising, in a cosmetically acceptable medium, at least one sulfate or sulfonate anionic surfactant, at least one amphoteric and/or zwitterionic surfactant and at least one particular amino silicone, the (amphoteric and/or zwitterionic surfactant)/(sulfate or sulfonate anionic surfactant) weight ratio ranging from 1:1 to 2:1, the total amount of surfactants representing from 4% to 35% by weight relative to the total weight of the final composition. The disclosure also relates to the use of the composition for protecting the coloration of, for example, artificially dyed hair.

21 Claims, No Drawings

DETERGENT COSMETIC COMPOSITIONS COMPRISING AT LEAST ONE AMINO SILICONE, AND USES THEREOF

This application claims benefit of U.S. Provisional Application No. 61/129,641, filed Jul. 9, 2008, the contents of which are incorporated herein by reference. This application also claims benefit of priority under 35 U.S.C. §119 to French Patent Application No. FR 0854634, filed Jul. 8, 2008, the contents of which are also incorporated herein by reference.

The present disclosure relates to novel cosmetic compositions with beneficial properties, intended for cleansing and protecting the color of keratin fibers such as the hair, and comprising, in a cosmetically acceptable aqueous support, at least one sulfate or sulfonate anionic surfactant, at least one surfactant chosen from amphoteric and zwitterionic surfactants, and at least one particular amino silicone, with a particular amphoteric and/or zwitterionic surfactant/sulfate or sulfonate anionic surfactant weight ratio. The disclosure also relates to processes using of the compositions for protecting the artificial color of dyed hair.

It is a known practice to dye keratin fibers, for example human keratin fibers such as the hair, with dye compositions comprising oxidation dye precursors, which are generally known as oxidation bases. These oxidation bases are colorless or weakly colored compounds, which, when combined with oxidizing products, give rise to colored compounds via a process of oxidative condensation. It is also known that the shades obtained with these oxidation bases can be varied by combining them with couplers or coloration modifiers. The variety of molecules used as oxidation bases and couplers allows a wide range of colors to be obtained.

It is also a known practice to dye keratin fibers by direct dyeing. The process conventionally used in direct dyeing comprises applying to keratin fibers direct dyes, which are colored and coloring molecules that have affinity for the fibers, in leaving them to stand and then in rinsing the fibers.

The colorations resulting therefrom can be chromatic colorations but may, however, only be temporary or semi-permanent; this can result from the nature of the interactions that bind the direct dyes to the keratin fiber and their desorption from the surface and/or the core of the fiber being responsible for weak dyeing power and poor fastness with respect to washing.

The artificial color of the hair afforded by a direct dyeing or oxidation dyeing treatment can gradually attenuate on repeated washing and can lead over time to fading of the coloration of the hair. The use of commercial rinse-out and leave-in care products may not sufficiently improve the fastness of the artificial color of the hair.

It could thus be useful to develop methods for protecting the artificial color from the effect of repeated washing, to do so under mild conditions that are compatible with dyed hair, and to improve the fastness of direct or oxidation dyeing, for example, with respect to shampoo washing.

Amino silicones have already been used for this purpose, as described in document EP 1 312 346.

The Applicant has found that the use of a detergent composition comprising a combination of surfactants and of at least one amino silicone may facilitate protection of the artificial color of keratin fibers with respect to repeated washing and thus improvement of the color fastness.

These findings form the basis of the present disclosure.

It has been found that by using the compositions according to the disclosure, the fading of the coloration after several shampoo washes can be limited. Thus, the loss of coloration, evaluated, for example, by the variation of the value of the coefficient DL* of locks before and after shampooing in the CIE L*a*b* system or alternatively by the DE* (corresponding to the square root of the sum of the squares of the variations of the coefficients L*, a* and b* of the locks before and after shampoo washing), can be reduced.

The compositions in accordance with the disclosure may also give keratin materials and for example the hair, a noteworthy treating effect that may be manifested, for example, by providing at least one of ease of disentangling, volume, lightness, smoothness, softness, or suppleness without any lank effect. The hair can look natural, clean, and non-greasy.

Thus, one subject of the present disclosure is novel detergent cosmetic compositions, characterized in that they comprise, in a cosmetically acceptable aqueous medium:
 (A) at least one sulfate or sulfonate anionic surfactant,
 (B) at least one surfactant chosen from amphoteric and zwitterionic surfactants, and
 (C) at least one amino silicone chosen from those of formulae (I) and (II),
 the (amphoteric and/or zwitterionic surfactant)/(sulfate or sulfonate anionic surfactant) weight ratio ranging from 1:1 to 2:1,
 the total amount of surfactants representing from 4% to 35% by weight relative to the total weight of the final composition.

A subject of the disclosure is also the cosmetic use of the above compositions for cleansing keratin fibers, for example, the hair.

Another subject of the disclosure thus relates to the use, as a pretreatment or as a post-treatment for oxidation dyeing or direct dyeing of human keratin fibers and including the hair, of a detergent composition as defined above for protecting the color with respect to washing of the artificially dyed keratin fibers.

A subject of the disclosure is also a process for protecting the color with respect to washing of artificially dyed keratin fibers, characterized in that it comprises applying to the fibers at least one detergent composition as defined above.

Another subject of the disclosure is also a process for protecting the color with respect to washing of artificially dyed keratin fibers, characterized in that it comprises applying to the fibers, before, during or after dyeing, at least one detergent composition as defined above.

The term "human keratin fibers" means head hair or bodily hairs, for example of the beard or moustache, the eyelashes and the eyebrows, and head hair.

The expression "artificially dyed keratin fibers" means keratin fibers that have been dyed via a direct dyeing process or via an oxidation dyeing process, for example via an oxidation dyeing process.

The term "washing" means at least one application to the keratin fibers of an aqueous rinse-out composition, which can be a detergent composition such as a shampoo. This term also includes swimming for example, in the sea or in a swimming pool.

The various subjects of the disclosure will now be detailed. All the meanings and definitions of the compounds used in the present disclosure given above and below are valid for all of the subjects of the disclosure.

(A) Sulfate or Sulfonate Surfactants:

According to the disclosure, the sulfate or sulfonate anionic surfactants are anionic surfactants comprising at least one sulfate ($-OSO_3H$ or $-OSO_3^-$) function and/or one sulfonate ($-SO_3H$ or $-SO_3^-$) function.

The sulfate or sulfonate anionic surfactants that may be used, alone or as mixtures, in the context of the present disclosure are salts (for example, alkali metal salts, such as of sodium, ammonium salts, amine salts, amino alcohol salts or magnesium salts) of alkyl sulfates, alkylamido sulfates, alkyl ether sulfates, alkylamido ether sulfates, alkylaryl ether sulfates, alkyl ether sulfosuccinates, acyl isethionates, or methyl acyl taurates; the alkyl or acyl radical of all these various compounds may in some embodiments contain from 8 to 24 carbon atoms, and the aryl radical may in some embodiments denote a phenyl or benzyl group.

The average number of ethylene oxide or propylene oxide groups may in some embodiments range from 2 to 50, for example, from 2 to 10.

Among these anionic surfactants, in some embodiments, $C_8$-$C_{14}$ or $C_{12}$-$C_{14}$ alkyl ether sulfate salts are used. These salts may in some embodiments comprise from 2 to 5 ethylene oxide groups.

In some embodiments, an anionic surfactant chosen from sodium, triethanolamine, magnesium or ammonium ($C_{12}$-$C_{14}$)alkyl sulfates, sodium, ammonium or magnesium ($C_{12}$-$C_{14}$)alkyl ether sulfates oxyethylenated with 2.2 mol of ethylene oxide, sodium cocoyl isethionate and methyltaurates may be used.

The sulfate or sulfonate anionic surfactants may in some embodiments be present in an amount ranging from 2% to 15% by weight, for example, from 4% to 8% by weight, or from 5% to 7% by weight relative to the total weight of the composition.

(B) Amphoteric and/or Zwitterionic Surfactant(s):

In some embodiments, the amphoteric and/or zwitterionic surfactants may be, without limitation, aliphatic secondary or tertiary amine derivatives in which the aliphatic radical is a linear or branched chain containing 8 to 22 carbon atoms and containing at least one water-soluble anionic group (for example carboxylate, sulfonate, sulfate, phosphate or phosphonate); mention may also be made of ($C_8$-$C_{20}$)-alkylbetaines, sulfobetaines, ($C_8$-$C_{20}$)alkylamido($C_1$-$C_6$)alkylbetaines or ($C_8$-$C_{20}$)alkylamido($C_1$-$C_6$)alkylsulfobetaines.

Among the amine derivatives, mention may be made of the products as described in U.S. Pat. No. 2,528,378 and U.S. Pat. No. 2,781,354 and having the structures:

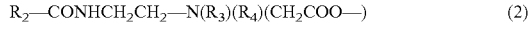

$$R_2\text{—CONHCH}_2\text{CH}_2\text{—N}(R_3)(R_4)(CH_2COO\text{—}) \quad (2)$$

in which: $R_2$—CO denotes a C6-C24 acyl radical, for example a radical present in hydrolysed coconut oil, an octyl, decoyl or dodecanoyl radical, and mixtures thereof, $R_3$ denotes a β-hydroxyethyl group and $R_4$ a carboxymethyl group; and

$$R_2\text{—CONHCH}_2\text{CH}_2\text{—N(B)(C)} \quad (3)$$

in which:
B represents —$CH_2CH_2OX'$, C represents —$(CH_2)_z$—Y', with z=1 or 2,
X' denotes the —$CH_2CH_2$—COOH group or a hydrogen atom,
Y' denotes —COOH or the —$CH_2$—CHOH—$SO_3H$ radical,
$R'_2$CO denotes a C6-C24 acyl radical, for example a radical present in hydrolysed coconut oil or linseed oil, or an octyl, decoyl or dodecanoyl, stearoyl, isostearoyl or oleoyl radical, and mixtures thereof.

These compounds are classified in the CTFA dictionary, 5th edition, 1993, under the names disodium cocoamphodiacetate, disodium lauroamphodiacetate, disodium caprylamphodiacetate, disodium capryloamphodiacetate, disodium cocoamphodipropionate, disodium lauroamphodipropionate, disodium caprylamphodipropionate, disodium capryloamphodipropionate, lauroamphodipropionic acid, and cocoamphodipropionic acid.

An example that may be mentioned is disodium cocoamphodiacetate, sold under the trade name Miranol® C2M Concentrate by the company Rhodia Chimie.

In some embodiments, at least one amphoteric and/or zwitterionic surfactant belonging to the betaine group is used, such as, for example, alkylbetaines, e.g., the cocoylbetaine sold under the name Dehyton AB 30 as an aqueous solution containing 30% AM by the company Cognis, or alkylamidobetaines, e.g., cocamidopropylbetaine, such as Tegobetaine® F50 sold by the company Goldschmidt.

In some embodiments, the at least one amphoteric and/or zwitterionic surfactant can be present in an amount ranging from 2% to 30% by weight, for example, from 5% to 10% by weight relative to the total weight of the composition.

The (amphoteric and/or zwitterionic surfactant)/(sulfate or sulfonate anionic surfactant) weight ratio ranges from 1:1 to 2:1. In some embodiments, it ranges from 1.2:1 to 1.8:1, from 1.3:1 to 1.5:1, or from 1.3:1 to 1.4:1.

In some embodiments, the composition may comprise at least one other surfactant for example at least one carboxylic anionic surfactant.

The said at least one carboxylic anionic surfactant may in some embodiments be present in concentrations ranging from 0.5% to 10% by weight, for example, from 1% to 5% by weight relative to the total weight of the composition.

In some embodiments, the total weight of surfactants may range from 4% to 35% by weight, for example from 6% to 25% by weight, or from 8% to 20% by weight relative to the total weight of the final composition.

(C) Amino Silicone:

The compositions of the present disclosure comprise at least one amino silicone chosen from those of formulae (I) and (II) below:

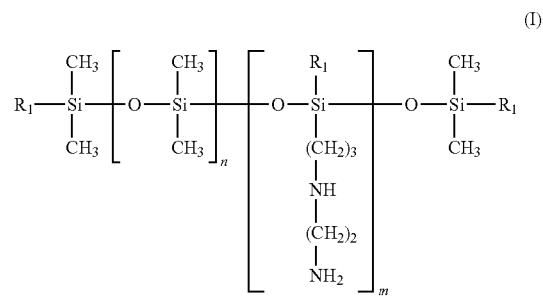

(I)

in which:
m and n are numbers such that the sum (n+m) can range in some embodiments from 1 to 1000, for example, from 50 to 250 or from 100 to 200, n denotes a number ranging from 0 to 999, for example from 49 to 249 or from 125 to 175 and m denotes a number from 1 to 1,000, for example from 1 to 10 or from 1 to 5, $R_1$, which may be identical or different, represents a hydroxyl or $C_1$-$C_4$ alkoxy radical, for example, the alkoxy radical may be a methoxy radical,
at least some of the radicals $R_1$ of the at least one silicone of formula (I) denoting an alkoxy radical.

The hydroxyl/alkoxy radical mole ratio of the silicone or of the mixture of silicones of formula (I) may in some embodiments range from 0.2:1 to 0.4:1, for example, from 0.25:1 to 0.35:1.

The weight-average molecular mass of the silicone may in some embodiments range from 2,000 to 1,000,000 Da, for example from 3,500 to 200,000 Da;

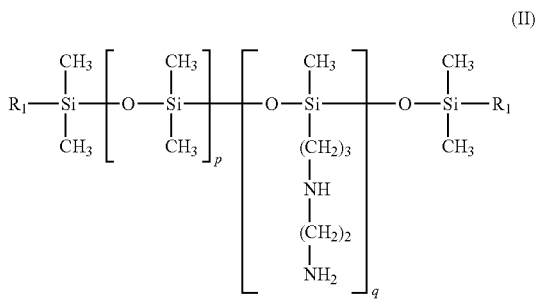

(II)

in which:
p and q are numbers such that the sum (p+q) can range in some embodiments from 1 to 1,000, for example from 50 to 350 or for example from 150 to 250,
p denotes a number from 0 to 999, for example from 49 to 349 or from 159 to 239, and q denotes a number from 1 to 1,000, for example from 1 to 10 or from 1 to 5;
$R_1$ represents a hydroxyl or $C_1$-$C_4$ alkoxy radical;
at least some of the radicals $R_1$ of the at least one silicone of formula (II) denoting an alkoxy radical.

The hydroxyl/alkoxy radical mole ratio of the at least one silicone of formula (II) can in some embodiments range from 0.1:1 to 5:1, for example, from 0.15:1 to 2:1 or from 0.5:1 to 0.9:1. In some embodiments, the alkoxy radical is a methoxy radical.

The weight-average molecular mass of the silicone may in some embodiments range from 2,000 to 200,000 Da, for example from 5,000 to 100,000 Da, or from 10,000 to 50,000 Da.

The weight-average molecular masses of these amino silicones can be measured by gel permeation chromatography (GPC) at room temperature, as polystyrene equivalents. The columns used are μ styragel columns. The eluent is THF and the flow rate is 1 ml/minute. 200 μl of a solution containing 0.5% by weight of silicone in THF are injected. Detection is performed by refractometry and UV-metry.

The commercial products corresponding to these silicones of structure (I) or (II) may include in their composition at least one other amino silicone whose structure is different from formula (I) or (II).

A product containing amino silicones of structure (I) is sold by the company Wacker under the name BELSIL® ADM 652.

A product containing amino silicones of structure (II) is sold by the company Wacker under the name FLUID WR 1300® or FLUID WR 1600®.

When these amino silicones are used, some embodiments involve using them in the form of an oil-in-water emulsion. The oil-in-water emulsion may comprise at least one surfactant.

The surfactants may be of any nature but may in some embodiments be cationic and/or nonionic.

The number-average size of the silicone particles in the emulsion can in some embodiments range from 3 nm to 500 nm.

In some embodiments, microemulsions with a mean particle size ranging from 5 nm to 60 nm or from 5 nm to 50 nm are used.

Thus, the amino silicone microemulsions of formula (II) sold under the names FINISH CT 96 E®, Wacker-Belsil ADM LOG 1 from Wacker or SLM 28020® by the company Wacker may be used in some embodiments.

In some embodiments, the at least one amino silicone is chosen such that the contact angle with water of a hair treated with a composition containing 2% (active material) of the silicone ranges from 90° to 180°, and for example, from 90° to 130°.

To measure the contact angle, the at least one amino silicone is dissolved or dispersed in a solvent for the at least one amino silicone or for the at least one amino silicone emulsion (hexamethyldisiloxane or water depending on the hydrophilicity of the silicone).

In some embodiments, the composition containing the at least one amino silicone chosen from those of formulae (I) and (II) is such that the contact angle with water of a hair treated with the composition ranges from 90° to 180°, for example from 90° to 130°.

The contact angle measurement is based on immersing a hair in distilled water. It consists in evaluating the force exerted by the water on the hair during its immersion in distilled water and during its removal. The forces thus measured are directly related to the contact angle θ between the water and the surface of the hair. The hair is said to be hydrophilic when the angle θ ranges from 0 to 90°, and hydrophobic when this angle ranges from 90° to 180°.

The test is performed with locks of natural hair that have been bleached under the same conditions and then washed.

Each 1 g lock is placed in a crystallizing dish 75 mm in diameter and then uniformly covered with 5 mL of the test formulation. The lock is thus left for 15 minutes at room temperature and then rinsed with distilled water for 30 seconds. The drained lock is left to dry in the open air until it is completely dry.

For each evaluation, 10 hairs that have undergone the same treatment are analyzed. Each sample, attached to a precision microbalance, is immersed via the end in a container filled with distilled water. This DCA ("Dynamic Contact Angle Analyser") balance, from the company Cahn Instruments, allows measurement of the force (F) exerted by the water on the hair.

In parallel, the perimeter of the hair (P) is measured via observation under a microscope.

The mean wettability force on ten hairs and the cross section of the analyzed hairs allows the contact angle of the hair on water to be determined, according to the formula:

$$F = P\lceil lv * \cos \theta$$

in which F is the wettability force expressed in newtons, P is the perimeter of the hair in meters, ⌈lv is the liquid/vapor interface tension of the water in $J/m^2$ and θ is the contact angle.

The product SLM 28020 from Wacker at 12% in water (i.e. 2% amino silicone) gives a contact angle of 93° according to the test indicated above.

The product Belsil ADM 652 from Wacker at 2% in hexamethyldisiloxane (i.e. 2% amino silicone) gives a contact angle of 111° according to the test indicated above.

In some embodiments, the composition contains at least one amino silicone of formula (II).

The at least one amino silicone chosen from those of formulae (I) and (II) may be used, in some embodiments, in an amount ranging from 0.01% to 20% by weight relative to the total weight of the composition, for example, from 0.05% to 10% by weight, or from 0.1% to 5% by weight relative to the total weight of the composition.

In some embodiments, the composition may also comprise at least one water-soluble salt and/or a water-soluble monohydroxylated or polyhydroxylated alcohol. The water-soluble salts according to the disclosure can in some embodiments be chosen from the salts of monovalent and divalent metals and of a mineral and organic acid.

Mention may be made, for instance, of sodium chloride, potassium chloride, calcium chloride, magnesium sulfate, sodium citrate and the sodium salts of phosphoric acid.

Water-soluble monohydroxylated or polyhydroxylated alcohols that may be mentioned include, for example, ethanol, isopropanol, propylene glycol, glycerol and hexylene glycol.

In some embodiments, the detergent compositions have a final pH ranging from 2 to 8, for example, from 3 to 7.5. The pH may be adjusted to the desired value conventionally by adding a base (organic or mineral) to the composition, for example, sodium hydroxide, aqueous ammonia or a primary, secondary or tertiary (poly)amine, for instance, monoethanolamine, diethanolamine, triethanolamine, isopropanolamine or 1,3-propanediamine, or alternatively by adding a mineral or organic acid, for example citric acid or hydrochloric acid.

The cosmetically acceptable aqueous medium may be constituted solely of water or of a mixture of water and of at least one cosmetically acceptable solvent, for example, the monohydroxylated or polyhydroxylated alcohols mentioned above or ethers of these alcohols, esters or ketones.

In some embodiments, the composition comprises at least 30% by weight, for example from 50% to 90% by weight or from 70% to 85% by weight of water relative to the total weight of the composition.

The composition can in some embodiments comprise less than 20% by weight of fatty phase relative to the total weight of the composition.

The fatty phase comprises all the fatty substances of the composition that are insoluble in water at room temperature, such as, for example, fatty esters, plant, mineral or synthetic oils, fatty alcohols, fatty acids, fatty amides, waxes and silicones. The fatty phase may in some embodiments range from 0.1% to 15% by weight, for example from 0.5% to 10% by weight or from 0.5% to 8% by weight, relative to the total weight of the composition.

The compositions may in some embodiments contain, in addition to the combination defined above, at least one viscosity regulator, such as a thickener. Mention may be made of scleroglucans, xanthan gums, fatty acid alkanolamides, alkyl ether carboxylic acid alkanolamides optionally oxyethylenated with up to 5 mol of ethylene oxide, such as the product sold under the name Aminol A15 by the company Chem Y, crosslinked polyacrylic acids and crosslinked acrylic acid/$C_{10}$-$C_{30}$ alkyl acrylate copolymers. These viscosity regulators can be used in the compositions in proportions that may be up to 10% by weight relative to the total weight of the composition. Crosslinked polyacrylic acids, for instance Carbopol 980 from Noveon, may also be used in some embodiments.

The compositions may also contain up to 5% of at least one nacreous agent and/or opacifier such as those that are well known in the state of the art, for instance fatty alcohols, sodium palmitate or magnesium palmitate, sodium or magnesium stearate or hydroxystearate, fatty alcohols, fatty-chain acyl derivatives such as ethylene glycol or polyethylene glycol distearates, fatty-chain ethers, for instance distearyl ether or 1-(hexadecyloxy)-2-octadecanol, and cyclodextrins, for instance, β-cyclodextrins.

The compositions may also optionally contain other agents which have the effect of improving the cosmetic properties of the hair or the skin without, however, impairing the stability of the compositions. Mention may be made in this respect of cationic surfactants, anionic, nonionic, cationic or amphoteric polymers, proteins, protein hydrolysates, ceramides, pseudoceramides, plant oils, fatty acids, for example containing linear or branched $C_{16}$-$C_{40}$ chains such as 18-methyl-eicosanoic acid, hydroxy acids, vitamins, provitamins such as panthenol, volatile or non-volatile silicones other than the amino silicones of formulae (I) or (II), which are soluble or insoluble in the medium, UV-screening agents, moisturizers, antidandruff or anti-seborrhoeic agents, hair-loss counteractants and free-radical scavengers, and mixtures thereof.

In some embodiments, the composition also comprises at least one non-silicone cationic polymer.

The cationic polymers that may be used may be chosen from any of those already known per se as improving the cosmetic properties of hair treated with detergent compositions, for example those described in patent application EP-A-0 337 354 and French patent applications FR-A-2 270 846, 2 383 660, 2 598 611, 2 470 596 and 2 519 863.

Even more generally, for the purposes of the present disclosure, the term "cationic polymer" denotes any polymer containing cationic groups and/or groups that can be ionized into cationic groups.

The cationic polymers that may be used may in some embodiments have a cationic charge density of greater than or equal to 0.01 meq./g, for example, ranging from 0.1 to 10 meq./g or from 3 to 8 meq./g.

In some embodiments, at least one cationic polymer may be used that is chosen from cationic polysaccharides, for example quaternary cellulose ether derivatives such as the products sold under the name Ucare Polymer JR 400 by the company Amerchol, cyclopolymers such as diallyldimethylammonium salt homopolymers, including, Merquat 100, and copolymers of a diallyldimethylammonium salt and of acrylamide, e.g., the chlorides sold under the names Merquat 550 and Merquat S by the company Nalco, guar gums modified with 2,3-epoxypropyltrimethyl-ammonium chloride, sold, for example, under the name Jaguar C13S by the company Rhodia Chimie, optionally crosslinked homopolymers and copolymers of (meth)acryloyloxyethyltrimethylammonium salt, sold by the company Ciba as a 50% solution in mineral oil under the trade names Salcare SC92 (crosslinked copolymer of methacryloyloxyethyltrimethylammonium chloride and of acrylamide) and Salcare SC95 (crosslinked homopolymer of methacryloyloxyethyltrimethylammonium chloride), quaternary copolymers of vinylpyrrolidone and of a vinylimidazole salt such as the products sold by BASF under the names Luviquat FC 370, Luviquat FC 550, Luviquat FC 905 and Luviquat HM-552.

In some embodiments, the at least one cationic polymer can be present in an amount ranging from 0.005% to 10% by weight, for example from 0.01% to 5% by weight or from 0.1% to 3% by weight relative to the total weight of the final composition.

In some embodiments, the composition may also contain at least one foam synergist such as $C_{10}$-$C_{18}$ 1,2-alkanediols or $C_{10}$-$C_{18}$ fatty alkanolamides derived from monoethanolamine or from diethanolamine.

Needless to say, a person skilled in the art will take care to select this or these optional additional compound(s) and/or the amounts thereof such that the stability of the composition and the cosmetic properties intrinsically associated with the composition in accordance with the disclosure are not, or are not substantially, adversely affected by the envisaged addition(s).

In some embodiments, the composition may be transparent.

The transparency may be measured by measuring the transmittance at 700 nm via a spectrometer (for example a Lambda 14 spectrometer from Perkin-Elmer or a UV2101PC spectrometer from Shimadzu). The transparent compositions have a transmittance of greater than or equal to 94%, and for example ranging from 96% to 100%.

These compositions may be in the form of more or less thickened liquids, creams or gels, and they can be suitable for washing and caring for keratin fibers, for example, the hair.

A subject of the disclosure is also a process for washing and conditioning keratin fibers, for example, the hair, which comprises applying to the wet keratin materials an effective amount of a composition as defined above, and then in rinsing with water after an optional leave-in time.

The compositions according to the disclosure can be used as shampoos for washing and conditioning the hair, and they are applied, in this case, to wet hair in amounts that are suitable to wash them, and the lather generated by massaging or rubbing with the hands is then removed after an optional leave-in time, by rinsing with water, the operation possibly being repeated one or more times.

Concrete but in no way limiting examples illustrating the disclosure are given below.

EXAMPLE 1

The following shampoo composition in accordance with the disclosure was prepared.

|  | 1 |
|---|---|
| Sodium lauryl ether sulfate (70/30 C12/C14) containing 2.2 mol of ethylene oxide, as an aqueous solution containing 70% AM | 5.6 g AM |
| Cocobetaine at 30% AM (Dehyton AB 30 from Cognis) | 7.5 g AM |
| Lauryl ether carboxylic acid at 90% AM in water (AKYPO RLM 45 CA from Kao) | 2.7 g AM |
| Amino silicone (Wacker-Belsil ADM LOG 1 from Wacker Silicones) | 1.35 g AM |
| Polydimethyldiallylammonium chloride in water at 40% active material (MERQUAT 100 from Nalco) | 0.24 g AM |
| Sodium chloride | 1 g |
| Cetylstearyl alcohol oxyethylenated with 60 EO 1,2-myristyl glycol ether (ELFACOS GT 282 S from Akzo Nobel) | 3.3 g |
| Fragrance, preserving agent | qs |
| Hydrochloric acid, qs pH | 5.3 |
| Demineralized water, qs | 100 g |

Hair treated with this composition disentangled easily and is light and smooth from the root to the end.

Artificially dyed hair treated with this composition had good color fastness with respect to repeated shampooing.

EXAMPLE 2

The following shampoo compositions were prepared:

|  | 2 (disclosure) | A |
|---|---|---|
| Sodium lauryl ether sulfate (70/30 C12/C14) containing 2.2 mol of ethylene oxide, as an aqueous solution containing 70% AM | 5.56 g AM | 7 g AM |
| Cocobetaine at 30% AM (DEHYTON AB 30 from Cognis) | 7.5 g AM | 2.5 g AM |
| Amino silicone (Wacker-Belsil ADM LOG 1 from Wacker Silicones) | 1.5 g AM | 1.5 g AM |
| Hydroxyethylcellulose quaternized with 2,3-epoxypropyl trimethylammonium (UCARE Polymer JR 400 from Amerchol) | 0.4 g AM | 0.4 g AM |
| Ethylene glycol distearate | 1.5 g | 1.5 g |
| Acrylic polymer emulsion (AQUA SF1 from Noveon) | 0.8 g AM | 0.8 g AM |
| Preserving agent | qs | qs |
| Citric acid or NaOH, qs pH | 5.5 | 5.5 |
| Demineralized water, qs | 100 g | 100 g |
| (Amphoteric and/or zwitterionic surfactant)/(sulfate anionic surfactant) weight ratio | 1.35:1 | 0.36:1 |

After eight shampoo washes (0.4 g of shampoo per g of hair), a DE (color difference before and after treatment by the 8 shampoo washes) of 8.75 was obtained on permanent-waved natural hair containing 90% grey hairs dyed with a Majirouge 6.66 dye from L'Oréal (4 g of cream and 6 g of 20-volumes oxidizing agent), as opposed to a DE of 13.3 obtained for hair treated with shampoo A. The smaller the value of DE, the more efficient the protection.

Thus, artificially dyed hair treated with composition 2 containing a ratio according to the present disclosure showed better color fastness with respect to repeated shampooing than that treated with composition A.

What is claimed is:

1. A detergent cosmetic composition, characterized in that it comprises, in a cosmetically acceptable aqueous medium:

(A) at least one sulfate or sulfonate anionic surfactant, (B) at least one surfactant chosen from amphoteric and zwitterionic surfactants, the (amphoteric and/or zwitterionic surfactant)/(sulfate or sulfonate anionic surfactant) weight ratio ranging from 1.3:1 to 2:1 and the total amount of surfactants representing from 6% to 25% by weight relative to the total weight of the final composition, (C) at least one amino silicone chosen from those of formulae (I) and (II) below:

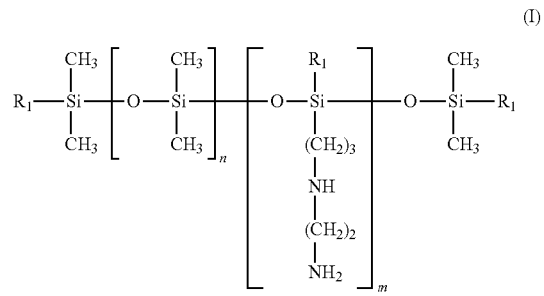

(I)

in which:

m and n are numbers such that the sum (n+m) ranges from 1 to 1,000, and at least one of the $R_1$ groups, which may be identical or different, represents $C_1$-$C_4$ alkoxy radical, the other $R_1$ group being either a hydroxyl or $C_1$-$C_4$ alkoxy radical;

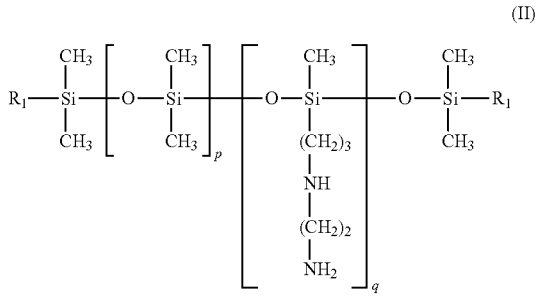

(II)

in which:
p and q are numbers such that the sum (p+q) ranges from 1 to 1,000, and
at least one of the $R_1$ groups, which may be identical or different, represents a $C_1$-$O_4$ alkoxy radical, the other $R_1$ group being either a hydroxyl or $C_1$-$C_4$ alkoxy radical,
wherein the at least one amino silicone is present in an amount ranging from 0.01% to 10% by weight relative to the total weight of the final composition, and
(D) at least one non-silicone cationic polymer.

2. The composition according to claim 1, characterized in that the at least one sulfate or sulfonate anionic surfactant is present in a concentration ranging from 2% to 15% by weight, the at least one amphoteric and/or zwitterionic surfactant is present in a concentration ranging from 5% to 10% by weight relative to the total weight of the final composition, and the (amphoteric and/or zwitterionic surfactant)/(sulfate or sulfonate anionic surfactant) weight ratio ranges from 1.3:1 to 1.8:1.

3. The composition according to claim 1, characterized in that it comprises at least one amino silicone of formula (I) in which the sum (n+m) ranges from 100 to 200.

4. The composition according to claim 1, characterized in that it comprises at least one amino silicone of formula (I) in which n denotes a number ranging from 125 to 175 and m denotes a number ranging from 1 to 10.

5. The composition according to claim 1, characterized in that it comprises at least one amino silicone of formula (II) in which the sum (p+q) ranges from 150 to 250.

6. The composition according to claim 1, characterized in that it comprises at least one amino silicone of formula (II) in which p denotes a number ranging from 159 to 239 and q denotes a number ranging from 1 to 10.

7. The composition according to claim 1, characterized in that the (amphoteric and/or zwitterionic surfactant)/(sulfate or sulfonate anionic surfactant) weight ratio ranges from 1.3:1 to 1.5:1.

8. The composition according to claim 1, characterized in that, in the at least one amino silicone chosen from those of formulae (I) and (II), the $C_1$-$C_4$ alkoxy radicals are methoxy radicals.

9. The composition according to claim 1, characterized in that it comprises at least one amino silicone of formula (I) in which the mole ratio of the hydroxyl/alkoxy radicals of the at least one amino silicone of formula (I) ranges from 0.2:1 to 0.4:1.

10. The composition according to claim 1, characterized in that it comprises at least one amino silicone of formula (I) in which the mole ratio of the hydroxyl/alkoxy radicals of the at least one amino silicone of formula (I) ranges from 0.25:1 to 0.35:1.

11. The composition according to claim 1, characterized in that it comprises at least one amino silicone of formula (II) in which the mole ratio of the hydroxyl/alkoxy radicals of the at least one amino silicone of formula (II) ranges from 0.1:1 to 5:1.

12. The composition according to claim 1, characterized in that it comprises at least one amino silicone of formula (II) in which the mole ratio of the hydroxyl/alkoxy radicals of the at least one amino silicone of formula (II) ranges from 0.15:1 to 2:1.

13. The composition according to claim 1, characterized in that it comprises at least one amino silicone of formula (II) in which the mole ratio of the hydroxyl/alkoxy radicals of the at least one amino silicone of formula (II) ranges from 0.5:1 to 0.9:1.

14. The composition according to claim 1, characterized in that the at least one amino silicone chosen from those of formulae (I) and (II) is in the form of a microemulsion.

15. The composition according to claim 1, characterized in that the at least one amino silicone chosen from those of formulae (I) and (II) is present in a concentration ranging from 0.01% to 20% by weight relative to the total weight of the composition.

16. The composition according to claim 1, characterized in that the at least one amino silicone chosen from those of formulae (I) and (II) is present in a concentration ranging from 0.1% to 5% by weight relative to the total weight of the composition.

17. The composition according to claim 1, characterized in that it also comprises at least one carboxylic anionic surfactant.

18. The composition according to claim 1, characterized in that the at least one cationic polymer is chosen from diallyldimethylammonium salt homopolymers and cationic polysaccharides, wherein the at least one cationic polymer is present in a concentration ranging from 0.005% to 10% by weight relative to the total weight of the final composition.

19. The composition according to claim 1, characterized in that the at least one cationic polymer is chosen from diallyldimethylammonium salt homopolymers and cationic polysaccharides, wherein the at least one cationic polymer is present in a concentration ranging from 0.1% to 3% by weight relative to the total weight of the final composition.

20. A detergent cosmetic composition, characterized in that it comprises, in a cosmetically acceptable aqueous medium:
(A) at least one sulfate or sulfonate anionic surfactant present in a concentration ranging from 4% to 8% by weight relative to the total weight of the composition,
(B) at least one surfactant chosen from amphoteric and zwitterionic surfactants present in a concentration ranging from 5% to 10% by weight relative to the total weight of the composition, the (amphoteric and/or zwitterionic surfactant)/(sulfate or sulfonate anionic surfactant) weight ratio ranging from 1.3:1 to 1.5:1,
(C) at least one amino silicone chosen from those of formulae (I) and (II) below:

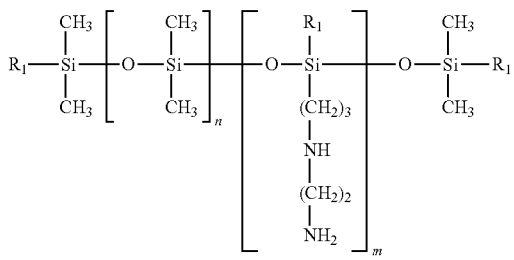

(I)

in which:
- m and n are numbers such that the sum (n+m) ranges from 100 to 200, m denoting a number ranging from 1 to 10, and
- at least one of the $R_1$ groups, which may be identical or different, represents a methoxy radical, the other $R_1$ group being either a hydroxyl or $C_1$-$C_4$ alkoxy radical,
- the mole ratio of the hydroxyl/alkoxy radicals of the at least one amino silicone of formula (I) ranging from 0.2:1 to 0.4:1;

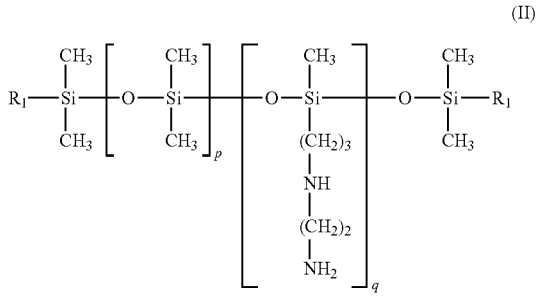

(II)

in which:
- p and q are numbers such that the sum (p+q) ranges from 150 to 250, q ranging from 1 to 10,
- at least one of the $R_1$ groups, which may be identical or different, represents a methoxy radical, the other $R_1$ group being either a hydroxyl or $C_1$-$C_4$ alkoxy radical,
- the mole ratio of the hydroxyl/alkoxy radicals of the at least one silicone of formula (II) ranging from 0.15:1 to 2:1;
- wherein the at least one amino silicone chosen from those of formulae (I) and (II) is present in the form of a microemulsion and in a concentration ranging from 0.1% to 5% by weight relative to the total weight of the composition,
- (D) at least one carboxylic anionic surfactant, and
- (E) at least one non-silicone cationic copolymer.

21. A process for protecting the color with respect to washing of artificially dyed keratin fibers, comprising applying to the fibers, before or after dyeing the fibers, at least one composition comprising, in a cosmetically acceptable aqueous medium,
- (A) at least one sulfate or sulfonate anionic surfactant,
- (B) at least one surfactant chosen from amphoteric and zwitterionic surfactants, the (amphoteric and/or zwitterionic surfactant)/(sulfate or sulfonate anionic surfactant) weight ratio ranging from 1.3:1 to 2:1 and the total amount of surfactants representing from 6% to 25% by weight relative to the total weight of the final composition, and
- (C) at least one amino silicone chosen from those of formulae (I) and (II) below:

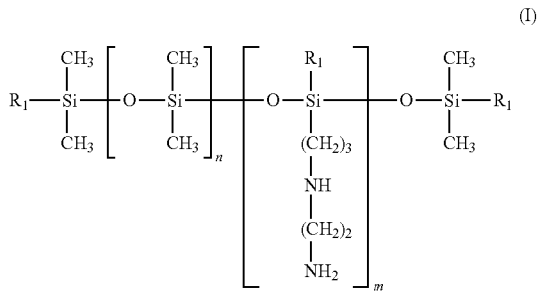

(I)

in which:
- m and n are numbers such that the sum (n+m) ranges from 1 to 1,000, and
- at least one of the $R_1$ groups, which may be identical or different, represents a $C_1$-$C_4$ alkoxy radical, the other $R_1$ group being either a hydroxyl or $C_1$-$C_4$ alkoxy radical;

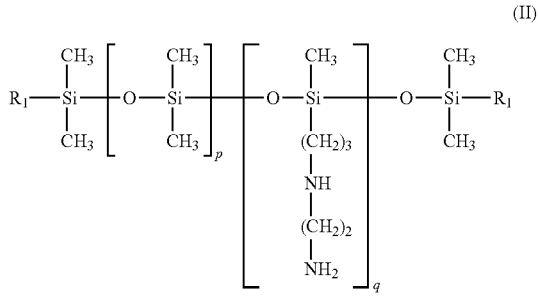

(II)

in which:
- p and q are numbers such that the sum (p+q) ranges from 1 to 1,000, and
- at least one of the $R_1$ groups, which may be identical or different, represents a $C_1$-$C_4$ alkoxy radical, the other $R_1$ group being either a hydroxyl or $C_1$-$C_4$ alkoxy radical, and
- (D) at least one non-silicone cationic polymer.

* * * * *

UNITED STATES PATENT AND TRADEMARK OFFICE
CERTIFICATE OF CORRECTION

PATENT NO.        : 8,476,212 B2
APPLICATION NO.   : 12/498582
DATED             : July 2, 2013
INVENTOR(S)       : Sandrine Decoster et al.

Page 1 of 1

It is certified that error appears in the above-identified patent and that said Letters Patent is hereby corrected as shown below:

In the Claims:

Claim 1, col. 11, line 22, "$C_1$-$0_4$" should be -- C1-C4 --.

Signed and Sealed this
Tenth Day of September, 2013

Teresa Stanek Rea
*Acting Director of the United States Patent and Trademark Office*